US00PP36302P2

(12) United States Plant Patent
Schniegenberg

(10) Patent No.: US PP36,302 P2
(45) Date of Patent: Dec. 10, 2024

(54) ***BUXUS* PLANT NAMED 'NSBBL'**

(50) Latin Name: ***Buxus* species**
Varietal Denomination: NSBBL

(71) Applicant: Spring Meadow Nursery, Inc., Grand Haven, MI (US)

(72) Inventor: Norman Schniegenberg, Richfield, OH (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/541,386

(22) Filed: Dec. 15, 2023

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ..... A01H 5/12; A01H 5/00; A01H 6/00
See application file for complete search history.

(56) References Cited

PUBLICATIONS

Sring Meadow Neatball Boxwood retrieved on Apr. 29, 2024 at https://springmeadownursery.com/plantfinder/neatball-buxus-06830, 2 pp. (Year: 2024).*
UPOV Pluto Apr. 19, 2024 retrieved on Apr. 29, 2024 at https://pluto.upov.int/result, one page. (Year: 2024).*

* cited by examiner

*Primary Examiner* — June Hwu
(74) *Attorney, Agent, or Firm* — Cassandra Bright

(57) ABSTRACT

A new and distinct cultivar of *Buxus* plant named 'NSBBL' is disclosed, characterized by large, round leaves maintaining deep green color throughout winter. Plants are very cold hardy with round, compact habits. The new cultivar is a *Buxus*, suitable for ornamental garden purposes.

3 Drawing Sheets

Figure 1:
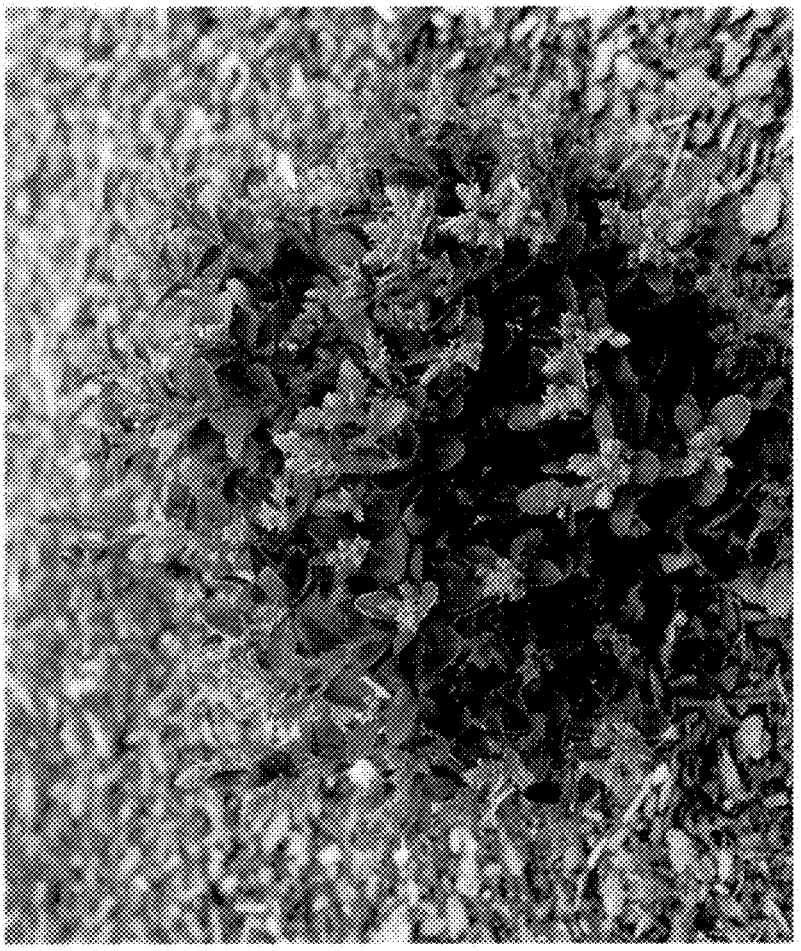

Latin name of the genus and species: *Buxus* species.
Variety denomination: 'NSBBL'.

BACKGROUND OF THE INVENTION

The new cultivar, hereinafter referred to as 'NSBBL', was discovered by the inventor as a single seedling plant growing among plants of various unpatented *Buxus* varieties in June 2015. 'NSBBL' was selected by the inventor among a group of container boxwood species in a bed at a nursery in Richfield, Ohio.

After identifying the new variety as a potentially interesting selection, the inventor first organized propagation of 'NSBBL' by softwood cuttings at a nursery in Richmond, Michigan in the fall of 2017. The inventor continued controlled testing and propagation, assessing stability of the unique characteristics of this variety. At least three generations have been reproduced and have shown that the unique features of this cultivar are stable and reproduced true to type.

The date of the first public disclosure was Jun. 27, 2023, occurring in Grand Haven, Michigan. This disclosure was made directly by the inventor or one who obtained the claimed invention directly or indirectly from the inventor. This sale and all public disclosures made between Jun. 27, 2023 and the filing of this application fall within the exception allowed under 102(b)(1).

SUMMARY OF THE INVENTION

The cultivar 'NSBBL' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'NSBBL' These characteristics in combination distinguish 'NSBBL' as a new and distinct *Buxus* cultivar:

1. Very cold hardy.
2. Foliage maintains deep green coloration throughout winter.
3. Large, round/obovate leaves.
4. Dense foliage with short internodes resulting in a round, compact habit.

COMPARISON TO PARENT VARIETY

The exact variety or species parents which the new cultivar originated from cannot be identified by the inventor. It is possible the seed parent variety is 'Green Velvet', however the inventor cannot be completely certain.

COMMERCIAL COMPARISON

'NSBBL' is similar in most horticultural characteristics to the unpatented commercial variety *Buxus* 'Winter Gem'. Plants of the new cultivar 'NSBBL' however, differ in the following:

1. Foliage of the new variety remains dark green throughout winter, while foliage of this comparator "bronzes" heavily in winter.
2. Plants of the new variety have a more densely-branched habit than plants of this comparator.

'NSBBL' is similar in most horticultural characteristics to the unpatented commercial variety *Buxus* 'Green Velvet'. Plants of the new cultivar 'NSBBL' however, differ in the following:

1. Foliage of the new variety is approximately 50% larger (in both length and width) than foliage of this comparator.
2. Foliage shape of the new variety is broad elliptic to globose; foliage shape of this comparator is narrowly elliptic.

BRIEF DESCRIPTION OF THE PHOTOGRAPHS

The accompanying photograph in FIG. 1 illustrates in full color a typical plant of 'NSBBL' grown outdoors in Grand Haven, Michigan. The plant is approximately 2 years old.

Figure 2:
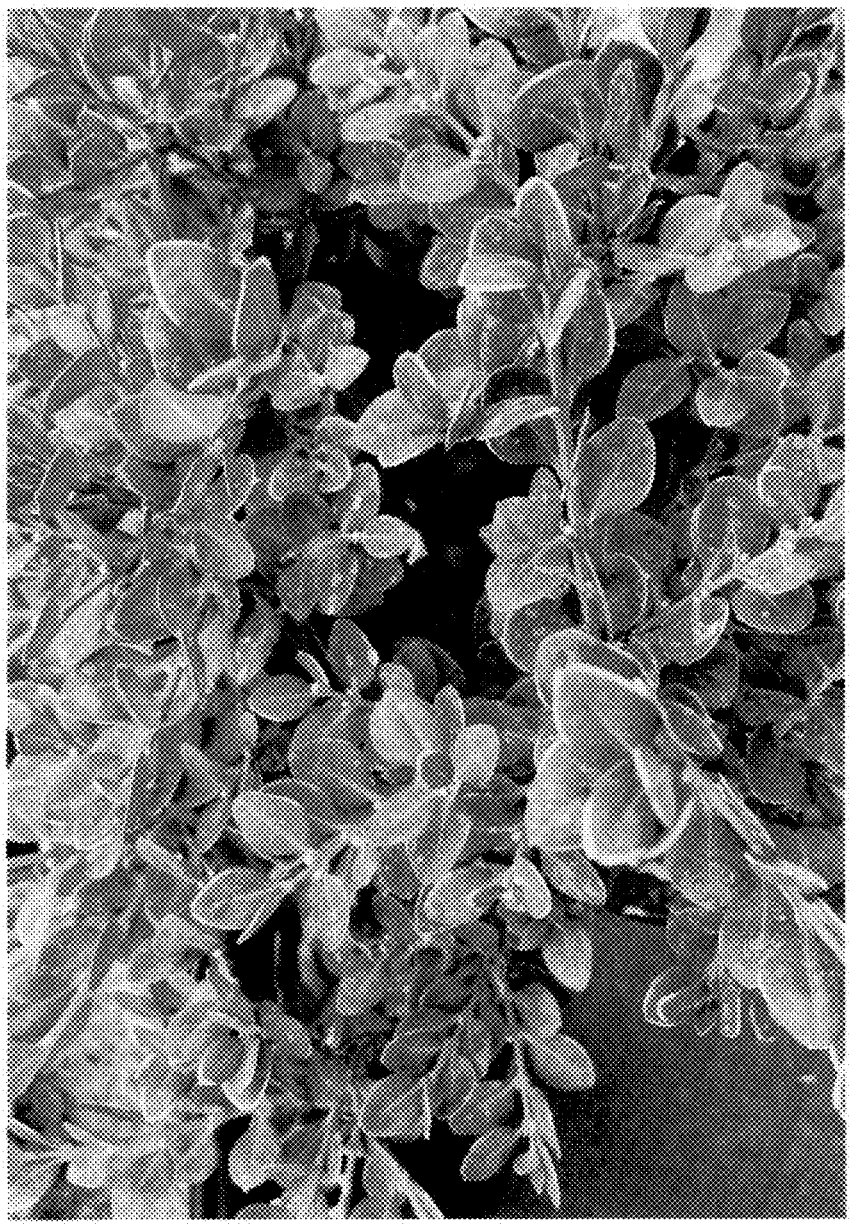

FIG. 2. is a closer view of the foliage and stems.

Figure 3:
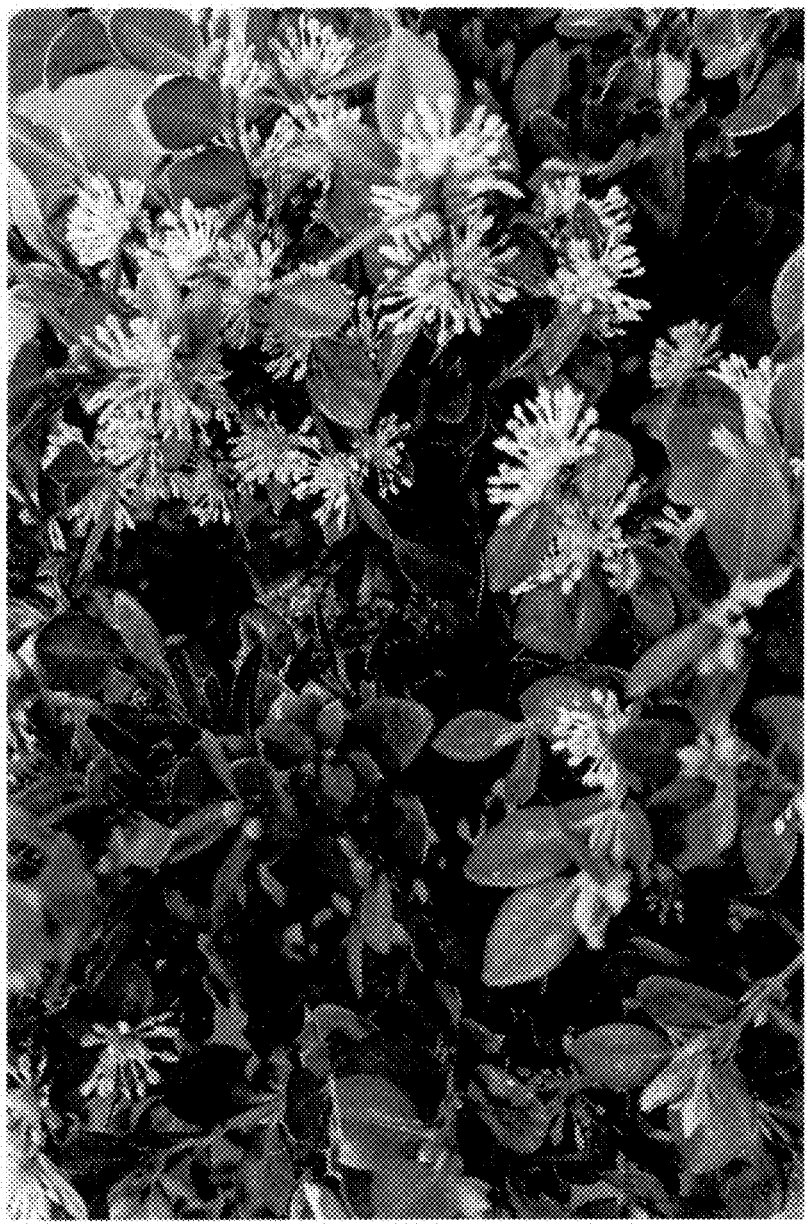

FIG. 3 is a close-view of the flowers and foliage.

The plant photographed has not been pruned and naturally grows as pictured. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'NSBBL' plants grown in a poly-greenhouse in Grand Haven, Michigan. Plants are approximately 3 to 4 years old, in a 3-gallon nursery container. Measurements and numerical values represent averages of typical plant types. Botanical classification: *Buxus* species 'NSBBL'.

PROPAGATION

Time to rooting: 30 days in summer, 45 days in winter at 18° C. to 27° C.

Time to produce a rooted young plant: 360 days in summer, 540 days in winter at 18° C. to 27° C.

Root description: Moderately dense, moderately free branching, fleshy, medium thickness. Light brown to tan in color, not accurately measured with R.H.S. chart.

PLANT

Growth habit: Upwards and outwards.
Plant shape: Rounded, mounding.
Height: 41 cm.
Plant spread: 38 cm.
Growth rate: Good.
Vigor: Quite vigorous.
Branching characteristics: Basal; some pinching required to encourage round habit.
Quantity of lateral branches: 6 to 8 main branches with about 10 branchlets each.
Length of lateral branches:
*Branches.*—24 cm.
*Branchlets.*—11.66 cm.
Diameter of lateral branches:
*Branches.*—7.33 mm.
*Branchlets.*—3.66 mm.
Internode length: Variable, 1.5 to 6 cm (internode length decreases from base to apex).

Stem:
*Shape.*—Rounded.
*Aspect.*—30 to 60°.
*Color.*—Young Stem: RHS Yellow-Green 144A. Mature Bark: RHS Grey-Brown 199A to 199B.
*Strength.*—Strong.
*Pubescence.*—None.

FOLIAGE

Leaf:
*Arrangement.*—Opposite, single.
*Shape of blade.*—Broad elliptic to globose.
*Length.*—Approximately 21.33 mm.
*Width.*—Approximately 11.33 mm.
*Apex.*—Acute.
*Base.*—Oblique.
*Attachment.*—Petiolate.
*Margin.*—Entire.
*Texture of top surface.*—Glabrous with a slightly waxy cuticle.
*Texture of bottom surface.*—Glabrous.
*Color.*—Young foliage upper side: RHS Yellow-Green N144C. Young foliage under side: RHS Yellow-Green N144C. Mature foliage upper side: RHS Green 139A to Yellow-Green 147A. Mature foliage under side: RHS Yellow-Green 144A. Winter foliage upper side: RHS Yellow-Green 147A. Winter foliage under side: RHS Yellow-Green 144A.
*Venation.*—Type: Pinnate. Venation Color: Non-distinct from leaf color.

Petiole:
*Length.*—Average 2.66 mm.
*Diameter.*—1 mm.
*Texture, upper side.*—Glabrous.
*Texture, under side.*—Glabrous.
*Color, upper side.*—RHS Yellow-Green 144A.
*Color, under side.*—RHS Yellow-Green 144A.

Other: Some branches may exhibit occasional marginal variegation approximately 1 mm in width; upper color RHS Yellow-Green 151B; lower color Yellow-Green 151D.

FLOWER

Flower:
*Flowering season.*—Early spring (April to May).
*Arrangement.*—Clusters of 5 flowers (fairly inconspicuous and lacking petals) emerging from lateral meristems.
*Habit.*—Flowering along the length of lateral branchlets.
*Shape.*—Petal-less, inconspicuous.
*Quantity of flowers per lateral stem.*—10 to 15 per branchlet.
*Quantity of buds per lateral stem.*—10 to 15.
*Quantity of flowers and buds per plant.*—Several hundred.
*Length.*—7 mm.
*Diameter.*—4 mm.
*Depth.*—7 mm.
*Persistence.*—Self-cleaning.
*Fragrance.*—Vaguely sweet and grassy, mild to moderate intensity.
*Aspect.*—Outward.

Bud:

*Shape*.—Ovoid.

*Length*.—3 mm.

*Diameter*.—2 mm.

*Color*.—RHS Yellow-Green N144A and N144C.

Sepals: Sepals are diminutive (less than 1 mm) and inconspicuous.

Peduncle: Flowers fuse directly to stem; peduncle is negligible.

REPRODUCTIVE ORGANS

Stamens:

*Quantity*.—4.

*Filament length*.—5 mm.

*Filament color*.—RHS Green-White 157A.

Anthers:

*Shape*.—Oblong, basifixed.

*Length*.—2 mm.

*Color*.—RHS Yellow 8B.

*Pollen*.—Amount: Abundant. Color: RHS Yellow 8B.

*Pistil*.—Quantity: 1. Length: 2 mm.

*Stigma*.—Shape: Irregular, globular. Color: RHS Yellow-Green 144C.

*Style*.—Length: Less than 1 mm. Color: RHS Yellow-Green 144C.

OTHER CHARACTERISTICS

Fruit and seeds: Not observed.

Disease and pest resistance: Neither resistance nor susceptibility to pests to normal diseases of *Buxus* have been observed.

Temperature tolerance: Tolerant from −31° C. to 38° C. Cold hardy to USDA zone 4B.

What is claimed is:

1. A new and distinct cultivar of *Buxus* plant named 'NSBBL' as herein illustrated and described.

* * * * *